(12) United States Patent
Keeley et al.

(10) Patent No.: US 8,834,446 B2
(45) Date of Patent: Sep. 16, 2014

(54) PULSATILE FLUX DRUG DELIVERY

(75) Inventors: Daniel J. Keeley, Boston, MA (US); Terri A. Kapur, Sharon, MA (US); Greg M. Schorn, Milford, MA (US)

(73) Assignee: Depuy Synthes Products, LLC, Raynham, MA (US)

(*) Notice: Subject to any disclaimer, the term of this patent is extended or adjusted under 35 U.S.C. 154(b) by 1124 days.

(21) Appl. No.: 12/137,923

(22) Filed: Jun. 12, 2008

(65) Prior Publication Data

US 2009/0312744 A1  Dec. 17, 2009

(51) Int. Cl.
*A61M 31/00* (2006.01)
*A61M 25/00* (2006.01)
*A61M 5/14* (2006.01)
*A61M 5/142* (2006.01)

(52) U.S. Cl.
CPC ....... *A61M 5/142* (2013.01); *A61M 2025/0042* (2013.01); *A61M 2005/1406* (2013.01); *A61M 2005/14208* (2013.01); *A61M 2210/0693* (2013.01)
USPC ........................................................ 604/506

(58) Field of Classification Search
USPC .................. 604/65–67, 93.01, 500, 503–508, 604/890.1, 891.1
See application file for complete search history.

(56) References Cited

U.S. PATENT DOCUMENTS

| | | | |
|---|---|---|---|
| 5,607,691 A | 3/1997 | Hale | |
| 6,090,072 A * | 7/2000 | Kratoska et al. | 604/164.01 |
| 6,395,292 B2 | 5/2002 | Peery | |
| 6,410,046 B1 | 6/2002 | Lerner | |
| 6,527,716 B1 | 3/2003 | Eppstein | |
| 6,635,268 B2 | 10/2003 | Peery | |
| 6,692,456 B1 | 2/2004 | Eppstein | |
| 6,706,032 B2 | 3/2004 | Weaver | |
| 6,770,729 B2 | 8/2004 | Van Antwerp | |
| 6,840,931 B2 | 1/2005 | Peterson | |
| 2003/0204181 A1 | 10/2003 | Starkebaum | |
| 2004/0077997 A1* | 4/2004 | Jasperson et al. | 604/67 |
| 2004/0215173 A1 | 10/2004 | Kunst | |
| 2005/0019251 A1 | 1/2005 | Hellerstein | |
| 2005/0177097 A1 | 8/2005 | Hildebrand et al. | |
| 2006/0020440 A1 | 1/2006 | Hellerstein | |
| 2006/0200069 A1 | 9/2006 | Cormier | |
| 2006/0204439 A1 | 9/2006 | Hellerstein | |
| 2006/0210614 A1 | 9/2006 | Quay | |
| 2006/0234203 A1 | 10/2006 | Lotan | |
| 2007/0093753 A1 | 4/2007 | Krulevitch | |
| 2007/0118093 A1 | 5/2007 | von Muhlen | |
| 2007/0276340 A1 | 11/2007 | Poston | |
| 2008/0009836 A1 | 1/2008 | Fiering | |

FOREIGN PATENT DOCUMENTS

| | | |
|---|---|---|
| WO | WO 2004033036 A2 | 4/2004 |
| WO | 2008020241 A2 | 2/2008 |

OTHER PUBLICATIONS

European Patent Application No. 09251548.5 Communication with Search Report dated Oct. 21, 2009.

Morrison, et al., Focal delivery during direct infusion to brain: role of flow rate, catheter diameter, and tissue mechanics; Am J Physiol. Oct. 1999; pp. R1218-R1229; 277 (4 Pt 2): Bethesda, MD.

(Continued)

*Primary Examiner* — Kami A Bosworth (57) ABSTRACT

A method of delivering a therapeutic fluid to the tissue of a mammal using pulsatile flux to prevent fluid backflow.

14 Claims, 10 Drawing Sheets

(56) References Cited

OTHER PUBLICATIONS

Krauze, Michal T.; Reflux-free cannula for convection-enhanced high-speed delivery of therapeutic agents; Nov. 2005; J Neurosurg 103:923-929.

Chen, Shi-Jian et al.; A realistic brain tissue phantom for intraparenchymal infusion studies; Aug. 2004; J Neurosurg 101:314-322.

* cited by examiner

PULSATILE FLUX DRUG DELIVERY

FIELD OF THE INVENTION

The present invention relates to methods of catheter-based drug delivery that are useful for the treatment and therapy of mammals. More specifically, the method comprises utilizing pulsatile flux to control delivery geometry while limiting the movement of local tissue away from the catheter shaft, thus preventing fluid backflow along the catheter track. The method is useful for the organ-specific delivery of therapeutic fluids, particularly in the brain.

BACKGROUND OF THE INVENTION

The use of catheters to deliver therapeutic fluids into the tissues of mammals is well known in the field of medicine. Catheters are used to deliver various therapeutic fluids to various tissues, including the delivery of pain medication to the spinal cord and brain, the delivery of anti-neoplastic agents to the brain, liver, and other tissues, and the delivery of various bioactive agents directly into the vasculature. The use of catheters to deliver therapeutic fluids directly into a target tissue provides several benefits over conventional routes of administration, including the elimination of gastric metabolism that occurs via oral administration. Another major benefit includes the use of less bioactive agent and the subsequent sparing of non-target tissues when the bioactive agents have undesirable side effects, such as highly toxic anti-neoplastic agents or highly specific proteins, growth factors, and gene therapy agents.

Some bioactive agents have great difficulty crossing the blood-brain barrier, requiring much higher levels to be obtained in the blood to achieve effective therapeutic concentrations in the brain. The use of drug delivery catheters implanted directly into the brain tissue has opened up the possibilities of using therapeutic agents for many neurological diseases and conditions that were previously untreatable.

Convection enhanced delivery (CED) utilizes fine intracranial catheters and low infusion rates of continuous injection under positive pressure to impart drugs directly into the extracellular space of the brain. First introduced by the National Institutes of Health in the 1990's, this technique has only recently been used for the treatment of brain cancer, and allows for a focused delivery of drugs to a specific target area. CED does not depend on diffusion, but relies on catheter design and a precisely controlled infusion rate to create a pressure gradient, along which a therapeutic agent passes directly into the extracellular space. This allows for a controlled homogenous distribution even for relatively large molecules such as proteins over large volumes of the brain and spinal cord.

Direct infusion into the brain by CED faces a number of challenges however, the most prominent being unpredictability of the distribution of the drug. The greatest contributor to the unpredictability is backflow of the infused agent along the catheter's insertion track. As the flow of infusate permeates the surrounding tissue, the tissue surrounding the catheter gradually experiences "creep" phenomena, whereby the fluid slowly flows alongside the exterior of the catheter, displacing the surrounding tissue until eventually the surrounding tissue no longer seals the catheter track and fluid reaches the entrance point of the catheter into the tissue. Upon reaching the entrance point, this fluid path alongside the catheter then becomes the path of least resistance and thus the primary path of fluid flow, creating an undesirable drug distribution to adjacent non-target tissues. For a discussion of CED see for example Morrison, et al., in Am J Physiol. 1999 October; 277 (4 Pt 2):R1218-29.

Others have attempted to overcome this limitation by incorporating various modifications to the catheter size, design, and materials. For example Krauze, et al., describe the use of a step-design cannula to limit or prevent backflow (J. Neurosurg 103:923-929, 2005). In PCT application publication WO 2008/020241A2 Gill, et al., describe the use of a stiff catheter shaft material to prevent vibrations and movement, and thus prevent backflow. In USPAP 2007/0276340A1 Poston, et al., describe the use of inflatable stents on the catheter shaft to create a seal in the tissue.

These mechanical modifications do not completely prevent backflow and also add complexity and cost to the catheter. Thus there is an ongoing need for a method to safely deliver a therapeutic fluid into the tissue of a mammal.

SUMMARY OF THE INVENTION

Methods of the present invention are comprised of using a drug pump to deliver a pulsatile flux of therapeutic fluid through a catheter placed in a distensible mammalian tissue, further comprising timing the pulsed intervals of fluid flow to efficiently deliver a therapeutic agent to target tissue while preventing the backflow of the fluid traveling along the catheter track to a non-target tissue. The backflow to non-target tissue is prevented by adjusting the timing of the pulses such that the distensible tissue has sufficient time to recover from the pressure wave of fluid delivery of the previous pulse, thereby maintaining or re-establishing a seal of the tissue around the catheter and thus preventing fluid backflow along the catheter track. Alternatively, the flow rate of the fluid can be modulated to achieve similar results. The geometry and volume of distribution can be modified by the size and number of delivery ports on the catheter, thereby maintaining a controlled delivery of drug to the target tissue.

DETAILED DESCRIPTION OF THE INVENTION

The present invention provides a method for the organ-specific, controlled delivery of a therapeutic fluid into a distensible tissue while preventing backflow of the fluid along the outer wall of the catheter. The method of the invention is useful for various types and designs of catheters, and is not limited by the type or design of catheter employed. The use of catheters to deliver therapeutic fluids into the CNS in particular has greatly reduced the amount of bioactive agent required for efficacy as compared with other routes of administration. However, due to unpredictable distribution geometries resulting from the backflow of fluid along the catheter track, complications can arise from the convection enhanced delivery of therapeutic agents.

For the purposes of distinctly and concisely pointing out the claimed invention, the definitions of several terms used will be useful. As described and used in this application, the term convection enhanced delivery, hereinafter referred to as CED, is understood to mean the delivery of a therapeutic fluid into a tissue by the bulk-flow resulting from establishing a positive pressure gradient of fluid in the tissue.

As described and used in this application, the term catheter is understood to mean a flexible tube having a substantially cylindrical shape, and further having a proximal end and a distal end connected by a shaft having hollow lumen through which fluid can flow. The term catheter as used herein is understood to include any and all variations thereof, including variations in the shape being less cylindrical and more oval, variations in the distal end of the catheter, such as variations in the size, shape, and materials of construction of the distal end, and also variations in the number, size, and geometrical location of holes (also called ports) in the distal end. The term catheter also includes variations in the materials of construction of the shaft, including the use of plastics, metals, ceramics, composite materials, fibers, filaments, powders, and particles.

Also included in the term catheter are variations in the basic design of the catheter, including the use of multiple lumens having additional functions such as for suction, for delivery of additional fluids different from the fluid delivered in the main lumen, or for housing one or more wires used for various functions, such as for navigation using a mechanical pullwire, for conduction and delivery of electrical energy for therapy, such as radio-frequency (RF) energy or DC current as might be applied to an electrode and directly to the tissue, or AC current such as might be used to power a transducer in the distal end, such as a piezoelectric ultrasonic transducer. Additional uses of a conductor in a multiple lumen could be for conduction of energy collected from the tissue or from a sensor located at the distal end of the catheter, such as a platinum electrode band as is commonly known in the art of electrophysiology.

As described and used in this application, the term cannula is understood to mean a non-flexible tube having a substantially cylindrical shape, and further having a proximal end and a distal end connected by a hollow lumen through which fluid can flow. The term cannula is understood to include any and all variations thereof, including variations in the distal portion of the cannula, such as variations in the shape of the tip, and also variations in the number, size, and geometrical location of holes in the distal tip, and also variations in materials, including the use of plastics, metals, ceramics, composite materials, fibers, filaments, powders and particles.

The major difference between a catheter and a cannula is one of rigidity. In common usage a catheter is flexible and made of one or more polymer materials, optionally reinforced with stainless steel wires or braided jacket embedded between layers of polymers, thereby providing for a strong flexible tube. In common usage a cannula is made of metal and is substantially rigid, providing little or no flexibility as compared to a catheter. A skilled physician will appreciate that certain applications may render the choice of a catheter or cannula superior to the other for a particular procedure, however either instrument may be used to deliver a therapeutic fluid in the method of the present invention without detracting from the inventive principles.

The major difference between a needle and a cannula is the sharpness of the distal tip. In common usage a cannula is made of metal providing for a rigid tube through which fluid can be delivered or aspirated, and typically has a blunt, square, or rounded distal tip to prevent trauma to tissue, whereas a needle has a sharpened tip for piercing tissue. In general a needle is typically smaller in diameter than a cannula, however either instrument may be used to deliver a therapeutic fluid in the method of the present invention without detracting from the inventive principles.

Analogously, a trocar consists of a metal cannula into which fits an obturator with a sharp three-cornered tip, which is withdrawn after the instrument has been inserted into a tissue. Thus, the terms catheter, needle, cannula, and trocar may all be used interchangeably for the purposes of the present invention, with the term catheter being the preferred term. It will be understood by one of ordinary skill in the art that the subtle differences in the size and rigidity of these devices do not affect the utility of the present invention.

The term catheter track as used in this application is understood to mean the path created in a tissue by inserting a catheter into the tissue and displacing the tissue to the outer wall of the catheter. As described above, the term catheter track and the term needle track are synonymous in the context of the present invention. The tissue surrounding the outer wall of the catheter can be juxtaposed directly against the outer wall of the catheter, effectively sealing the catheter track, or the tissue can be some distance away from the outer wall of said catheter, effectively creating a free annular space around the outer wall of the catheter. The void remaining in the tissue immediately after the removal of the catheter is still referred to as the catheter track. After a period of time the catheter track in the tissue can remain as an open space, but more typically it will heal and fill with native surrounding tissue, or with a remodeled tissue, such as scar tissue.

The term flow as used in this application is understood to mean the movement of a volume of fluid per unit of time, and has the units of microliters per minute ($\mu L/min$). The term flux as used in this application is understood as the amount of material that flows through a unit area per unit time. Thus in the flow of a therapeutic fluid having a concentration of therapeutic agent in mg/ml across a two-dimensional surface in mm×mm, flux has the units of milligrams per minute per square millimeter (mg/min·mm²). The term pulsatile flux as used in this application is understood to mean a flux per unit of time being comprised of a series of alternating periods of positive flux and substantially zero flux. The periods of zero flux are understood to not necessarily be absolutely zero flux, but rather may consist only of minor flux due to residual pressure in the system, as would be achieved by turning off the pump or pressure source. Alternatively, a pulsatile flux could be comprised of a series of alternating periods of high positive flux and low positive flux.

The term backflow as used in this application is understood to mean the undesired flow of fluid from the distal end of a catheter along the catheter track towards the proximal end of the catheter, resulting in fluid delivery to a non-target region of the tissue. As described and used in this application, the term backflow is synonymous with the term reflux, and the terms may be used interchangeably.

The term regimen as used in this application is understood to mean the series and sequences of pressure modulations of a fluid in a catheter over a period of time to create a pulsatile flux of the fluid at the distal end of the catheter. The term regimen is equivalent to the term "dose regimen" as used herein.

The term therapeutic fluid as used in this application is understood to mean a liquid administered to a mammal to provide a medical benefit. Such therapeutic fluids may or may not contain bioactive agents, for example isotonic saline solution may be considered a therapeutic fluid lacking any bioactive agents.

The term bioactive agent as used in this application is understood to mean a material that stimulates a biological response in a host organ, tissue, or cell. Examples of bioactive agents include, but are not limited to drugs, chemicals, pharmaceuticals, hormones, peptides, proteins, growth factors, signaling factors, deoxyribonucleic acids (DNA), and ribonucleic acids (RNA, iRNA).

CED makes it possible to distribute large volumes of therapeutic fluids and agents to target regions in the central nervous system. This approach alleviates many challenges that arise from treating various diseases and conditions that otherwise respond poorly systemic administration of these agents, or are surgically difficult to access or surgically inoperable.

The pumping of fluid during CED can be achieved manually such as with a syringe, but more preferably is performed automatically, such as with a syringe pump, peristaltic pump, or an implantable drug pump. Implantable drug pumps are known in the art and typically consist of piezoelectrically actuated pumps, diaphragm, bellows, piston, and peristaltic roller and tube type pumping mechanisms, all of which are contemplated by the present invention. Variations in the distal end of catheters are well known in the art, having multiple ports of various sizes and locations to modify and affect the fluid output of the catheter and the distribution zone of the therapeutic agent in the target tissue. Unfortunately, except at very low flux, the pressure gradient that is established in the tissue using the CED method is ultimately sufficient to displace the tissue in the catheter track and cause backflow of the therapeutic fluid. By using the pulsatile flux method of the present invention to deliver the therapeutic fluid, a pressure gradient is still formed that is sufficient to deliver a large molecule, such as a protein. This allows one to utilize a relatively higher flux than methods of continuous delivery and with the benefit of preventing backflow.

The flux may be affected by modifying the concentration of agent contained within the infusate, the infusate flow rate, and/or the relative surface area of the fluid flow output. By altering these variables individually or in combination a controllable geometry of drug distribution can be achieved.

Figure 1:
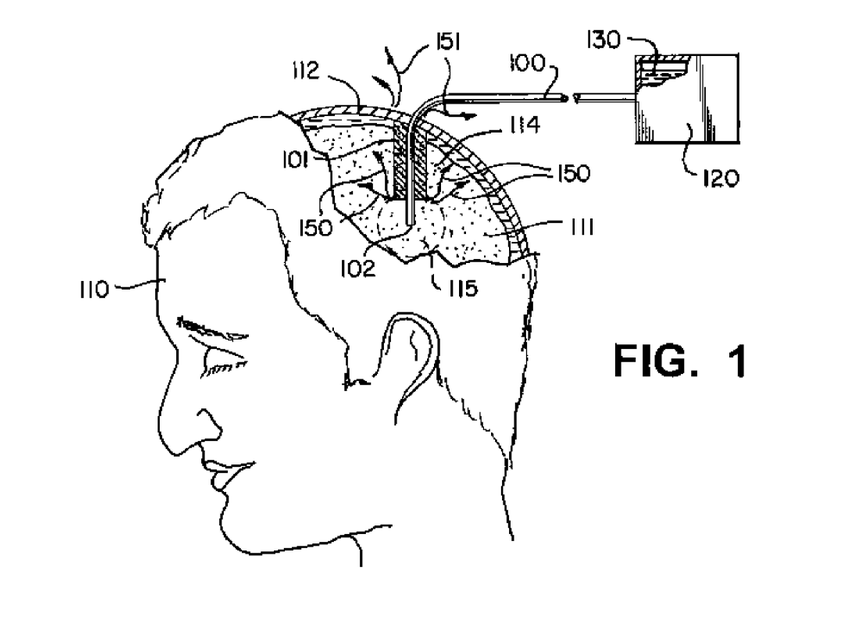
FIG. 1 depicts a drug delivery catheter placed in the brain of a human.

Referring now to the figures, FIG. 1 is a sectional view that shows a drug delivery catheter (100) placed into the brain (111) of a human (110), and connected to a drug pump (120) containing a therapeutic fluid (130). The drug delivery catheter (100) passes through the entry point in the cranium (112) and through non-target brain tissue (114), creating a catheter track (hatched region 101) in the adjacent non-target brain tissue (114). The distal end (102) of the catheter (100) is located deep within the brain, within and adjacent to the surrounding target tissue (115). During convection enhanced delivery the drug pump (120) pumps therapeutic fluid (130) through the lumen of the catheter (100) and out of the distal end (102) of the catheter into the surrounding target brain tissue (115). After a period of time the non-target brain tissue (114) displaces away from the catheter (100), thereby enlarging catheter track (101) and allowing therapeutic fluid (130) to backflow along the catheter track (101) into the adjacent non-target brain tissue (114) as indicated by arrows (150) and eventually up to and out of the entry point in the cranium (112), as indicated by arrows (151).

Figure 2:
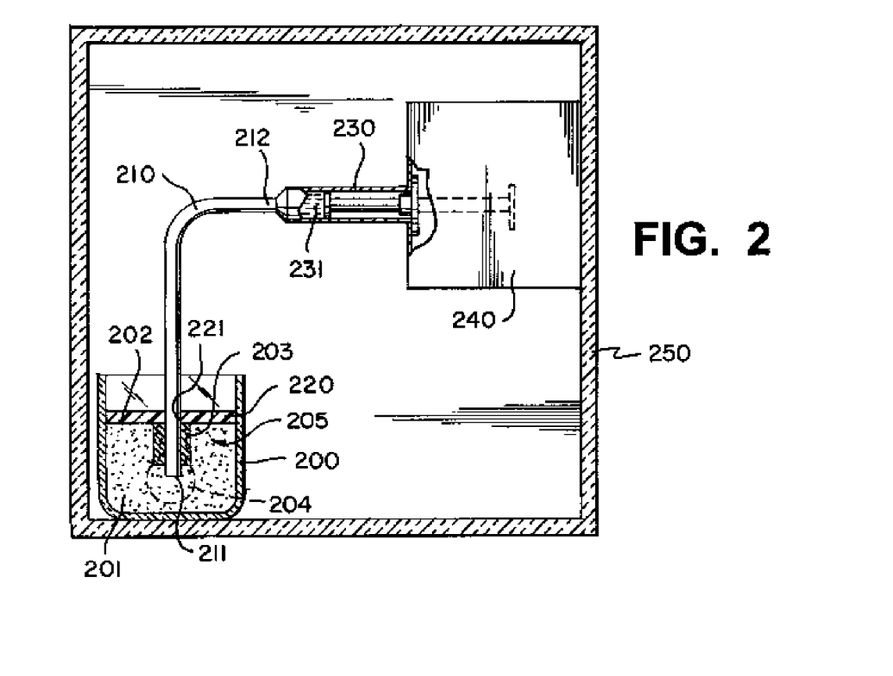
FIG. 2 depicts the experimental setup of examples 2-6.

Now referring to FIG. 2, which depicts a sectional view of the experimental setup of the examples. A beaker (200) contains agarose gel (201), into which a catheter (210) in inserted to a depth of approximately 38 mm from the surface (202) of the agarose gel, creating a catheter track (hatched region 203) in the agarose gel (201). The distal end (211) is located within the target area (204) of the agarose gel (201). A plastic holder (220) in the shape of a disc having a hole (221) in the center is placed on the surface (202) of the agarose gel, wherein the catheter (210) passes through the hole (221), thereby stabilizing the position of the distal end (211) of the catheter (210) in the agarose gel (201). The proximal end (212) of the catheter (210) is connected to a syringe (230) containing a fluorescent-labeled protein solution (231). The syringe (230) is mounted to a programmable syringe pump (240), and the entire setup consisting of the beaker (200) containing agarose gel (201), the catheter (210), the syringe (230) and the programmable syringe pump (240), are contained within an oven (250). The programmable syringe pump (240) is programmed to provide a pulsatile flux dose regimen of the fluorescent-labeled protein solution (231) according to the method of the present invention by pumping the fluorescent-labeled protein solution (231) through the catheter (210) to the distal end of the catheter (211) and out of the catheter ports (not shown) and into the target area (204) of the agarose gel (201) surrounding the distal end of the catheter. The occurrence of backflow would be observed by the presence of fluorescent-labeled protein solution (231) in the non-target area (205) surrounding the catheter track (203) and also at the surface (202) of the agarose gel.

Figure 3:
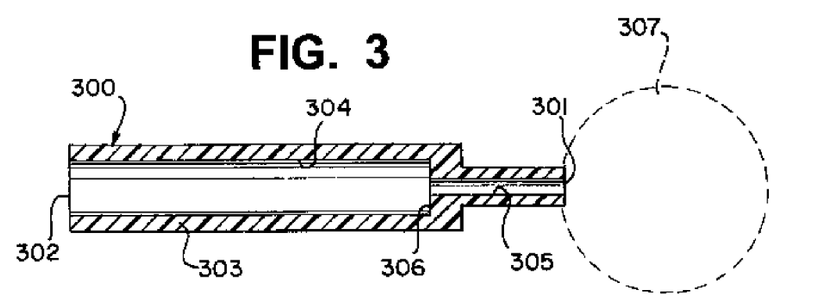
FIG. 3 depicts a cross-section view of a single port step-catheter.

FIG. 3 depicts a cross-sectional view of a single port step-catheter (300), having a distal end (301), a proximal end (302), and a shaft (303) having a lumen (304) through which fluid can flow. The distal end (301) has a single opening or port (305) through which fluid can exit the lumen (304) and flow into the surrounding area (307). Optionally as shown, the lumen (304) and also optionally the catheter shaft (305) can have a step (306) therein, wherein the diameter is reduced to enhance the fluid flow characteristics of the catheter.

Figure 4:
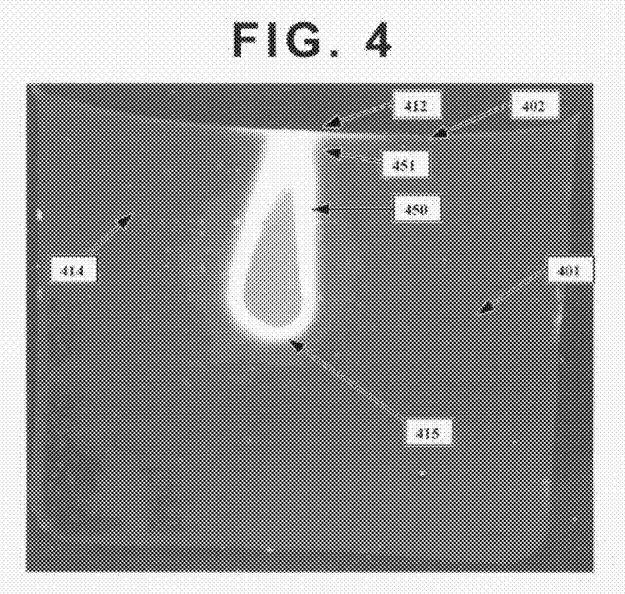
FIG. 4 shows the distribution zone of the fluorescent-labeled protein in the center section of the agarose gel obtained using a single-port catheter and a constant 1.0 µl/min. flow rate over 300 minutes of infusion, showing the backflow of fluid around the catheter track and up to the surface of the agarose gel.

FIG. 4 shows the distribution zone of fluorescent-labeled protein in a beaker of agarose gel obtained using the single-port step-catheter of FIG. 3 and a constant 1.0 μl/min. flow rate over 300 minutes of infusion. The agarose gel (401) was sectioned into approximately 2-mm sections to provide a cross-section of the catheter track (450). The agarose gel (401) contains a target area (415) and a non-target area (414) based on the position and placement of the distal end of the catheter, and contains an insertion point (412) where the catheter was inserted into the surface (402) of the agarose gel. The image shows the distribution of fluorescent-labeled protein in the target area (415), as well as backflow along the catheter track (450) located in non-target area (414) and into surrounding agarose gel (451) and up to the entry point (412).

Figure 5:
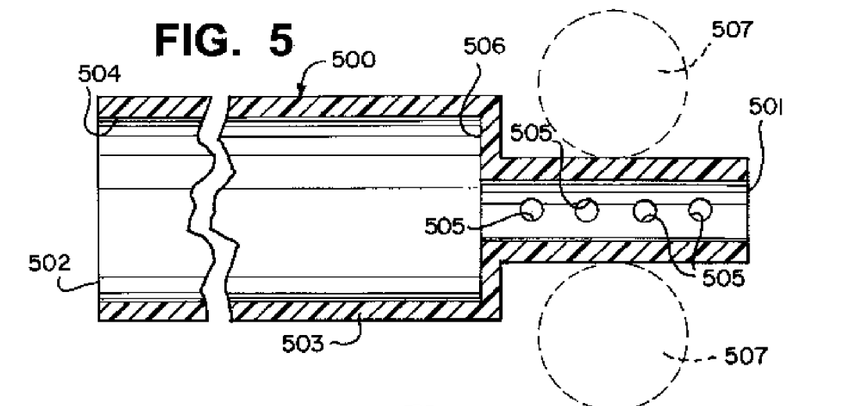
FIG. 5 depicts the port geometry of an 8-port catheter.

FIG. 5 is a cross-sectional view that depicts the port geometry of an 8-port step-catheter (500), having a distal end (501), a proximal end (502), and a shaft (503) having a lumen (504) through which fluid can flow. The distal end (501) has 8 ports (505), of which four are shown in the sectional view with the remaining four positioned 180 degrees opposite from the ones shown, through which fluid can exit the lumen (504) and flow into the surrounding area (507). Optionally, the lumen (504) and also optionally the catheter shaft (503) can have a step (506) therein, wherein the diameter is reduced to enhance the fluid flow characteristics of the catheter. Optionally, the lumen of the catheter distal tip (501) can be sealed off.

FIGS. 6a-e show various pulsatile flux regimens of the present invention. In an exemplary embodiment the pulsatile flux is comprised of three distinct intervals of time, herein denoted as steps. Now referring to FIG. 6a, the abscissa denotes the flow rate in µL/min and is fixed at 2.7 µL/min. Step 1 is indicated on the ordinate scale of time for 25 seconds. Thus, the pump is turned on for a period of 25 seconds of 2.7 µL/min flow. The pump is then turned off for a period of time of 375 seconds, as indicated by step 2. Thus steps 1 and 2 together constitute an interval of time of 400 seconds having an intermittent operation of the pump. Steps 1 and 2 are repeated wherein the flow is again turned on for a period of time of 25 seconds and again turned off for a period of time of 375 seconds. Now referring to FIG. 6b, the periodic time cycles of steps 1 and 2 comprising 25 seconds on and 375 seconds off is repeated for several repetitions over the course of a period of one hour. After one hour of intermittent pump operation the pump is turned off for one hour, as indicated by step 3. The periodic sequence of steps 1, 2, and 3 are repeated during the course of therapy to generate pulsatile flux having a regimen of 25/375/1 denoting time periods of 25 seconds on for step 1, 375 seconds off for step 2, and step 3 denoting one hour of repetition and one hour completely off.

Figure 6A:
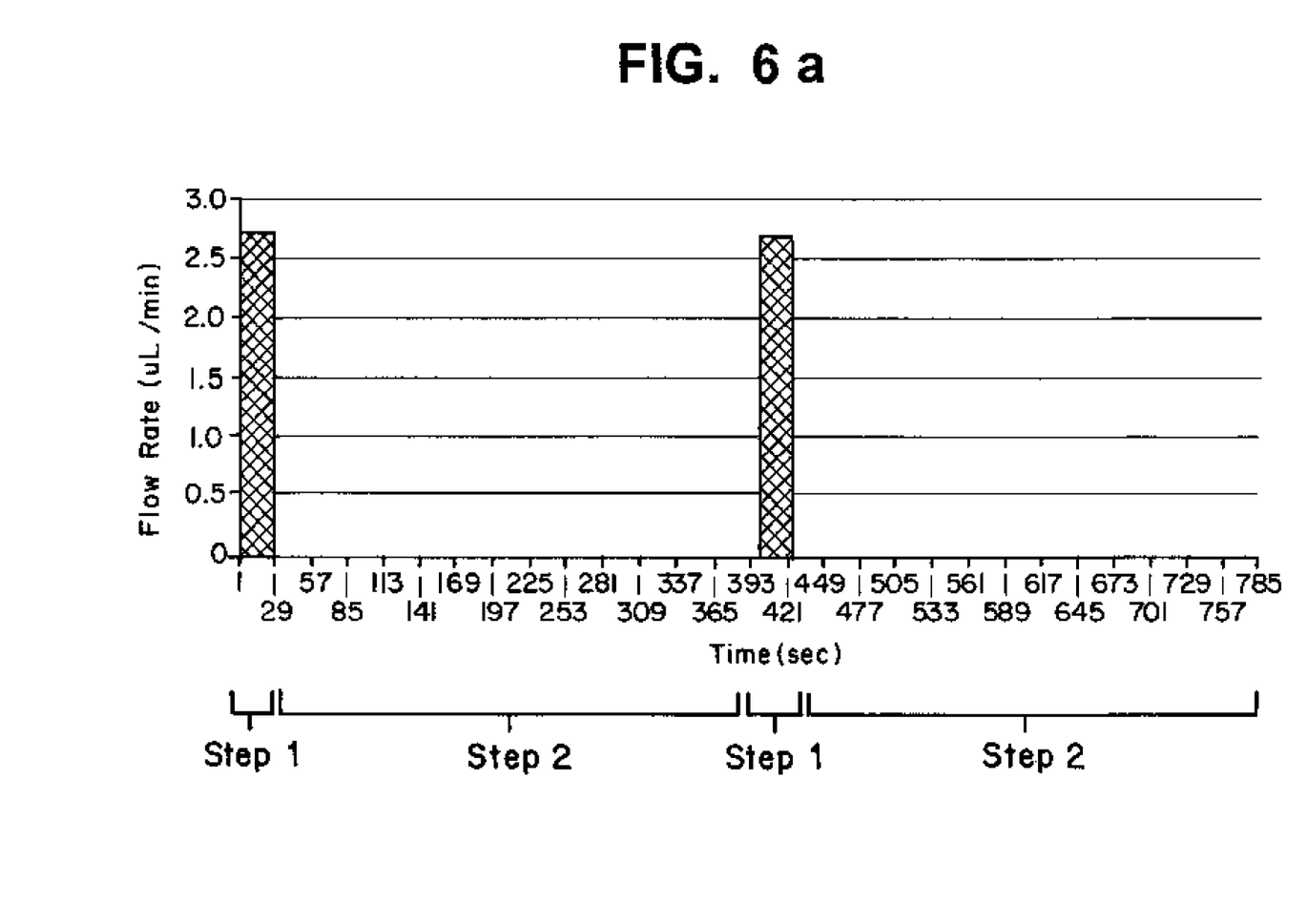
FIGS. 6a-e depict various embodiments of pulsatile flux regimens.
Figure 6B:
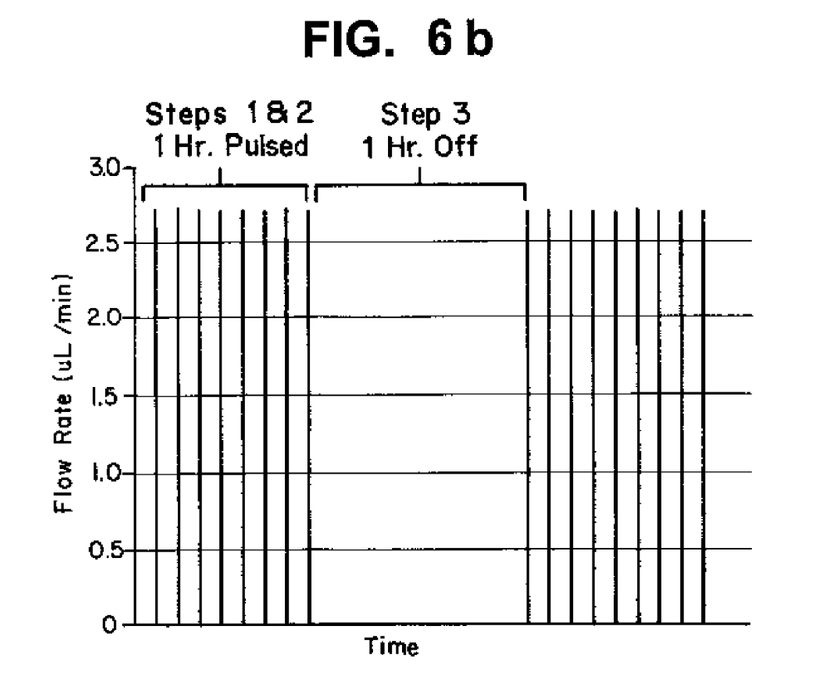
Figure 6C:
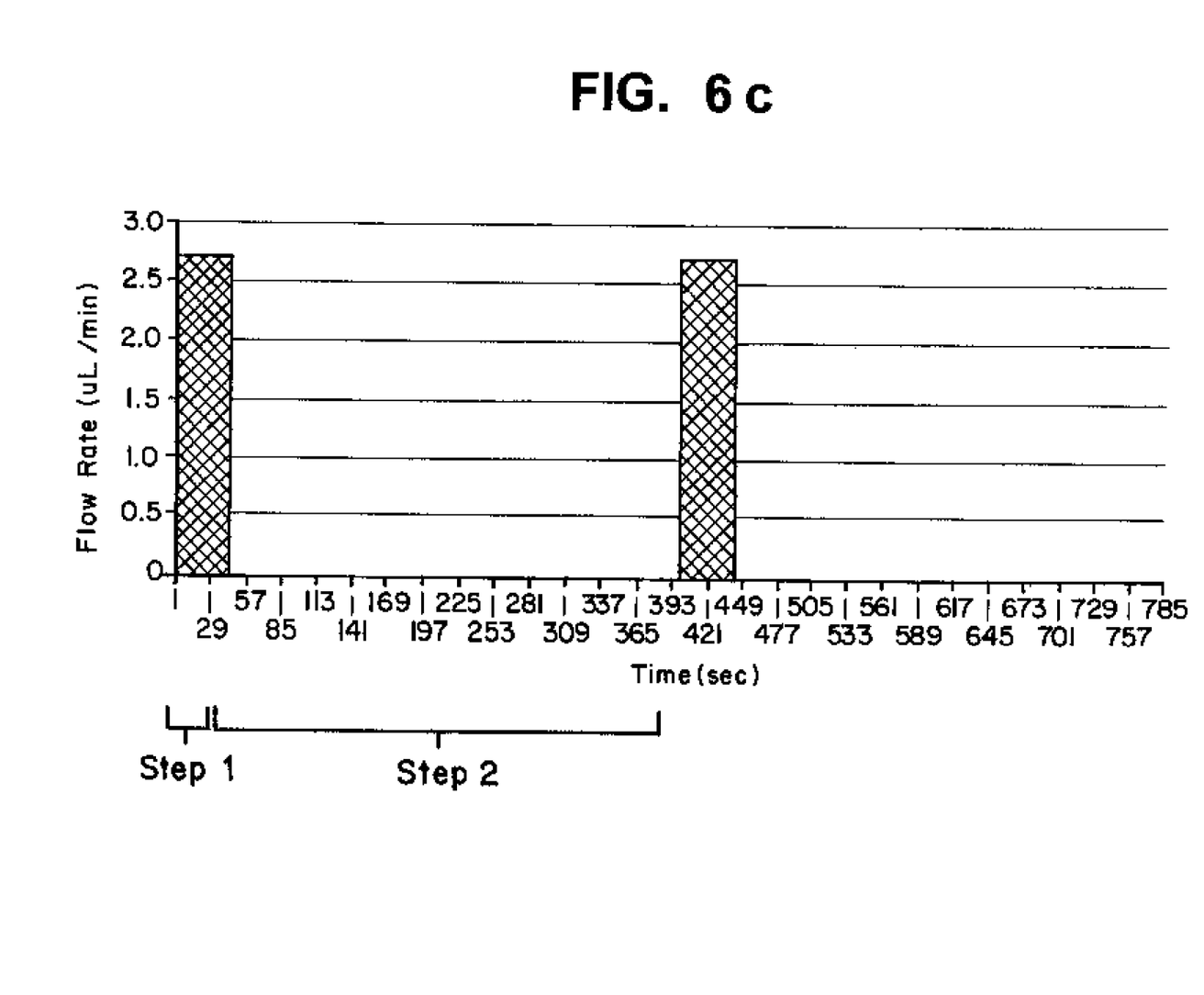
Figure 6D:
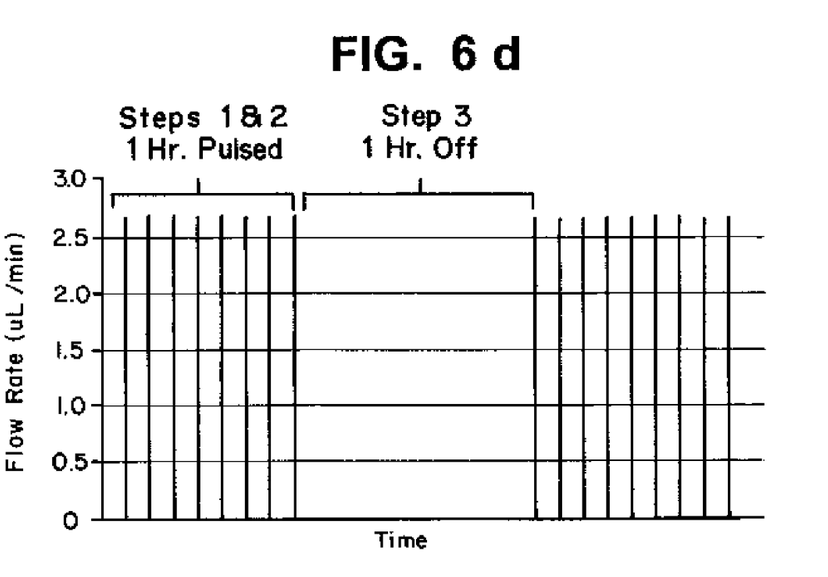

In an analogous manner, FIGS. 6c and 6d depict the steps 1, 2, and 3 of a 40/360/1 pulsatile flux regimen, wherein step 1 is 40 seconds on at 2.7 µL/min, step 2 is 360 seconds off, and step 3 is 1 hour.

Figure 6E:
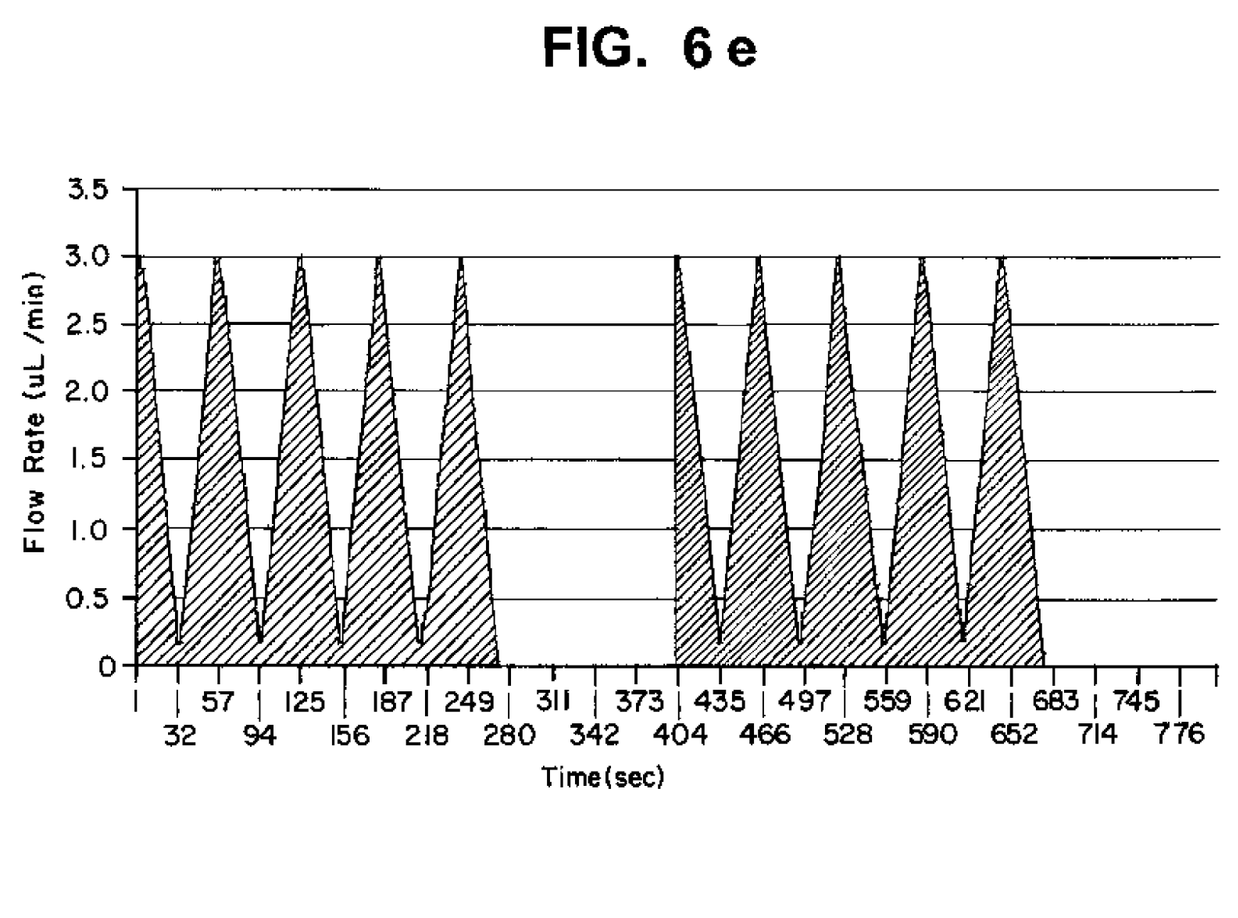

FIG. 6e depicts a variable flow rate regimen for steps 1 and 2 wherein the flow rate is turned on to 3.0 µL/min at the beginning of the first step in the series, and then is gradually ramped down to zero flow over 32 seconds, after which the flow is gradually ramped back up to 3.0 µL/min and then back down to zero, and the sequence repeated over the course of five minutes followed by a period of three minutes of zero flow.

These combinations are given as illustrative examples only, and it would be obvious to one of ordinary skill that there are countless numbers of permutations and complex combinations of steps, on and off cycles, flow rates, and ramp cycles that would be useful to generate the pulsatile flux of the present invention, and that the these various permutations are considered within the scope of the present invention.

Figure 7:
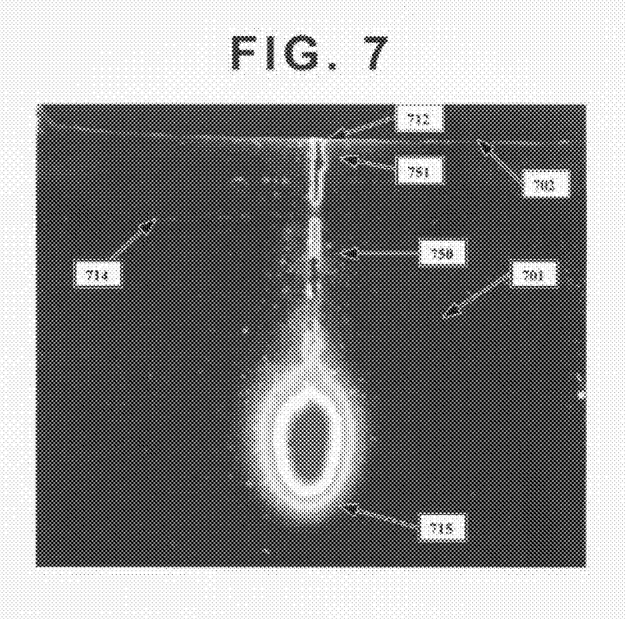
FIG. 7 shows the distribution zone of the fluorescent-labeled protein in agarose gel obtained using an 8-port catheter and the pulsatile flux pressure regimen of FIG. 6b over 24 hours of infusion.

FIG. 7 shows the distribution zone of fluorescent-labeled protein in a section of agarose gel obtained using an 8-port step-catheter (see FIG. 5) and the 25/375/1 pulsatile flux pressure regimen of FIG. 6b over 24 hours of infusion. The agarose gel (701) contains a target area (715) and a non-target area (714) based on the position and placement of the distal end of the catheter, and contains an insertion point (712) where the catheter was inserted into the surface (702) of the agarose gel. The image shows the distribution of fluorescent-labeled protein in the target area (715). The presence of fluorescent-labeled protein along the catheter track (750) is due to artifact from removal of the catheter. Note that compared with FIG. 4 and also with the target area (715) there is little or no fluorescent-labeled protein located in the agarose gel surrounding the catheter track (750) or in non-target area (714) or in the surrounding agarose gel (751) near the entry point (712).

Figure 8:
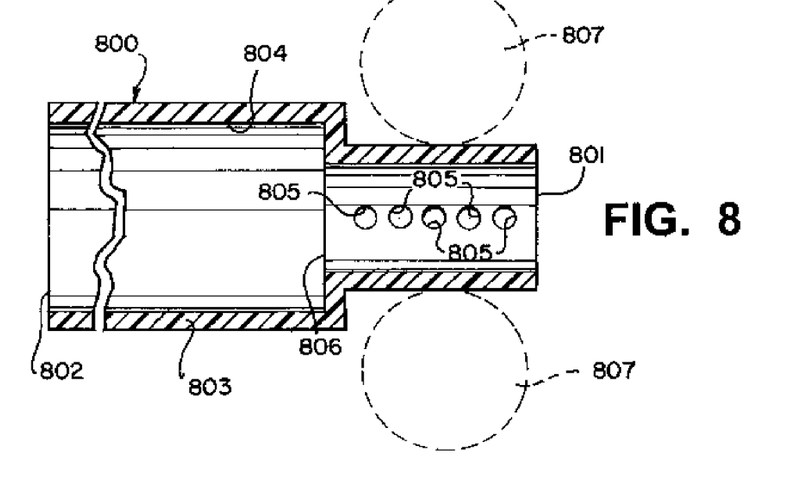
FIG. 8 depicts the port geometry of a 15-port catheter.

FIG. 8 is a cross-sectional view that shows the port geometry of a 15-port step-catheter (800), having a distal end (801), a proximal end (802), and a shaft (803) having a lumen (804) through which fluid can flow. The distal end (801) has 15 ports (805), of which five are shown in the sectional view with the remaining ten offset 60 and 120 degrees opposite from the ones shown, through which fluid can exit the lumen (804) and flow into the surrounding area (807). Optionally, the lumen (804) and also optionally the catheter shaft (805) can have a step (806) therein, wherein the diameter is reduced to enhance the fluid flow characteristics. Optionally, the lumen of the catheter distal tip (501) can be sealed off.

Figure 9:
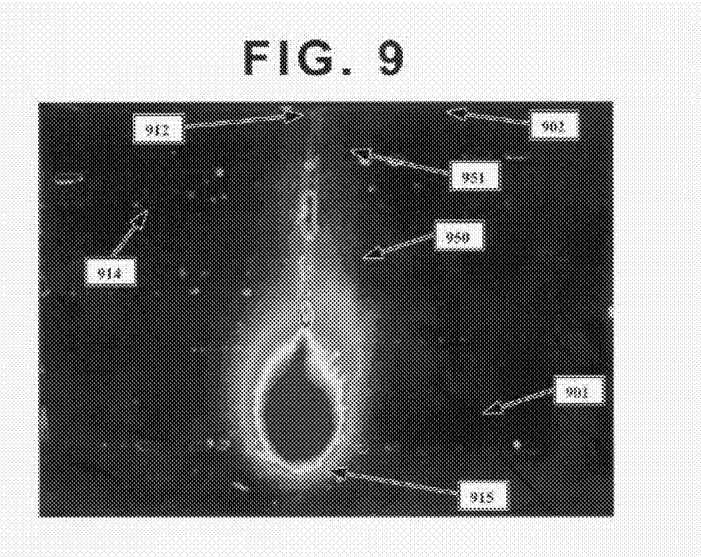
FIG. 9 shows the distribution zone of the fluorescent-labeled protein in agarose gel obtained using a 15-port catheter and the pulsatile flux pressure regimen of FIG. 6b over 24 hours of infusion.

FIG. 9 shows the distribution zone of fluorescent-labeled protein in a section of agarose gel obtained using a 15-port step-catheter (see FIG. 8) and the 25/375/1 pulsatile flux pressure regimen of FIG. 6b over 24 hours of infusion. The agarose gel (901) contains a target area (915) and a non-target area (914) based on the position and placement of the distal end of the catheter, and contains an insertion point (912) where the catheter was inserted into the surface (902) of the agarose gel. The image shows the distribution of fluorescent-labeled protein in the target area (915). The presence of fluorescent-labeled protein along the catheter track (950) is due to artifact from removal of the catheter. Note that compared with FIG. 4 and also with the target area (915) there is little or no fluorescent-labeled protein located in the agarose gel surrounding the catheter track (950) or in non-target area (914) or in the surrounding agarose gel (951) near the entry point (912).

Figure 10:
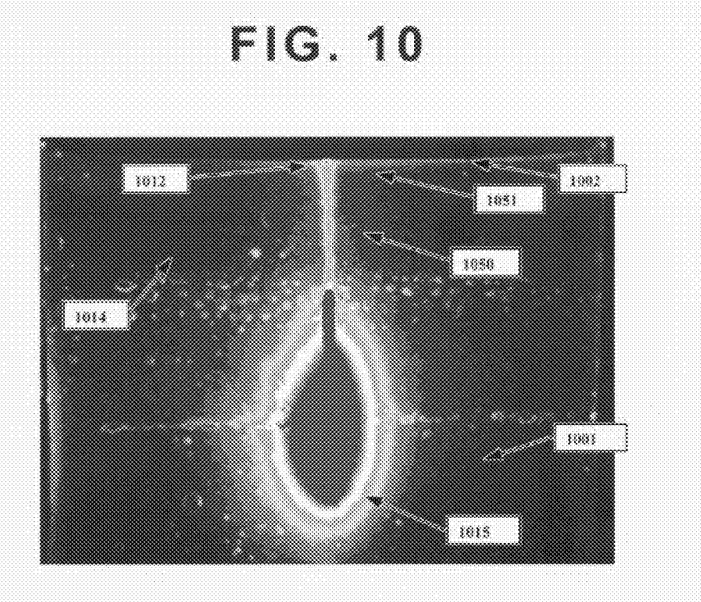
FIG. 10 shows the distribution zone of the fluorescent-labeled protein in agarose gel obtained using an 8-port step-catheter and the pulsatile flux pressure regimen of FIG. 6d over 24 hours of infusion.

FIG. 10 shows the distribution zone of fluorescent-labeled protein in a section of agarose gel obtained using an 8-port step-catheter and the 40/360/1 pulsatile flux pressure regimen of FIG. 6d over 24 hours of infusion. The agarose gel (1001) contains a target area (1015) and a non-target area (1014) based on the position and placement of the distal end of the catheter, and contains an insertion point (1012) where the catheter was inserted into the surface (1002) of the agarose gel. The image shows the distribution of fluorescent-labeled protein in the target area (1015). The presence of fluorescent-labeled protein along the catheter track (1050) is due to artifact from removal of the catheter. Note that compared with FIG. 4 and also with the target area (1015) there is little or no fluorescent-labeled protein located in the agarose gel surrounding the catheter track (1050) or in non-target area (1014) or in the surrounding agarose gel (1051) near the entry point (1012).

Figure 11:
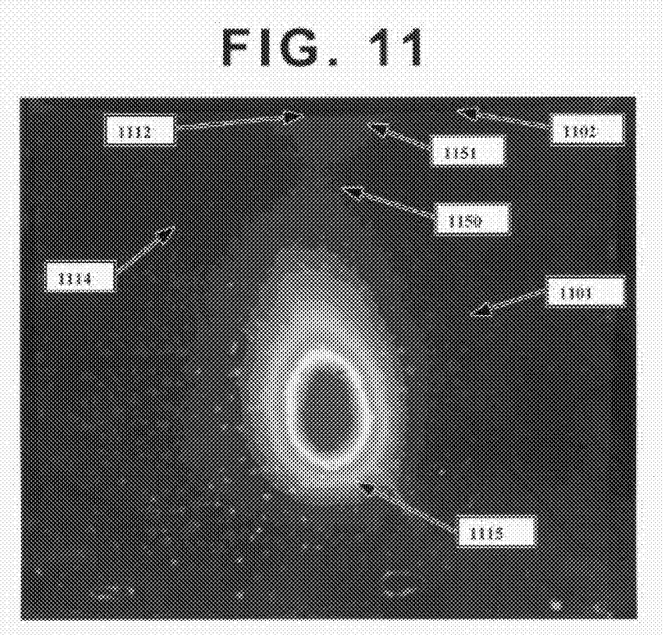
FIG. 11 shows the distribution zone of the fluorescent-labeled protein in agarose gel obtained using a 15-port step-catheter and the pulsatile flux pressure regimen of FIG. 6d over 24 hours of infusion.

FIG. 11 shows the distribution zone of fluorescent-labeled protein in a section of agarose gel obtained using a 15-port step-catheter and the 40/360/1 pulsatile flux pressure regimen of FIG. 6d over 24 hours of infusion. Although the agarose gel (1101) was similarly sectioned into approximately 2-mm sections to provide a cross-section of the catheter track (1150), the location of the sectioning in this example did not provide a clear indication of the void space of the catheter track. The agarose gel (1101) contains a target area (1115) and a non-target area (1114) based on the position and placement of the distal end of the catheter, and an insertion point (1112) where the catheter was inserted into the surface (1102) of the agarose gel. The image shows the distribution of fluorescent-labeled protein in the target area (1115). Note that compared with FIG. 4 and also with the target area (1115) there is little or no fluorescent-labeled protein located in the agarose gel surrounding the catheter track (1150) or in non-target area (1114) or in the surrounding agarose gel (1151) near the entry point (1112).

Figure 12A:
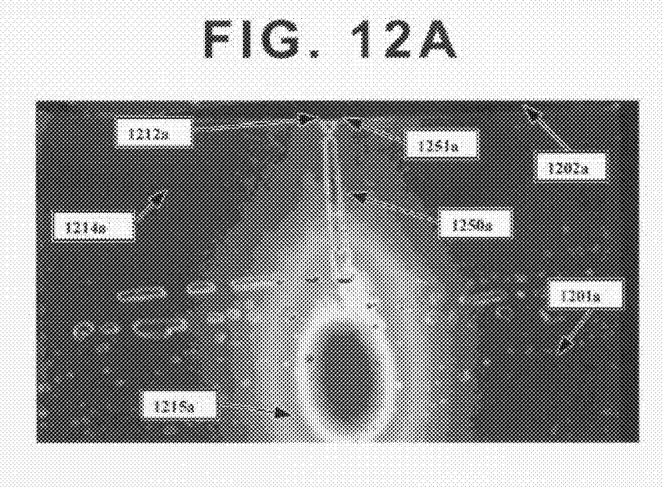
FIGS. 12a and 12b show the distribution zones of the fluorescent-labeled protein in agarose gels obtained using two different 15-port step-catheters and the pulsatile flux pressure regimen of FIG. 6b over 76 hours of infusion.
Figure 12B:
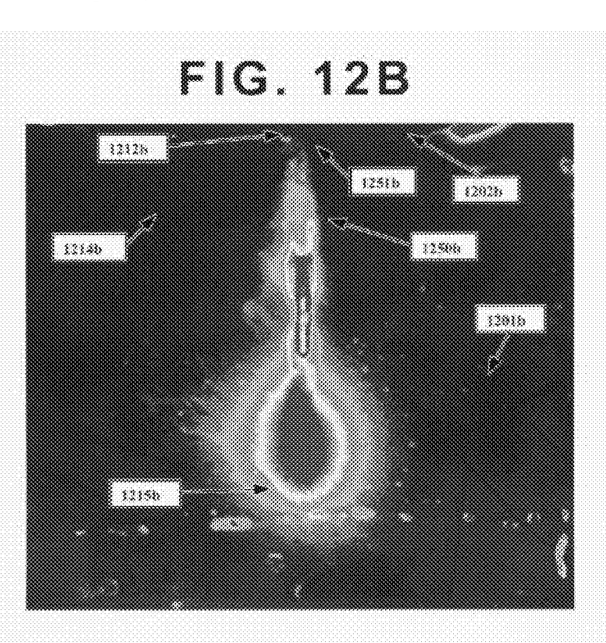

FIGS. 12a and 12b show the distribution zones of fluorescent-labeled protein in sections of agarose gel obtained using two different 15-port step-catheters and the 25/375/1 pulsatile flux pressure regimen of FIG. 6b over 76 hours of infusion. The agarose gels (1201a,b) were sectioned into approximately 2-mm sections to provide cross-sections of the catheter tracks (1250a,b). The agarose gels (1201a,b) contain target areas (1215 a,b) and non-target areas (1214 a,b) based on the position and placement of the distal ends of the catheters, and contain insertion points (1212a,b) where the catheters were inserted into the surface (1202a,b) of the agarose gels. The images show the distributions of fluorescent-labeled protein in the target areas (1215a,b).

Figure 13:
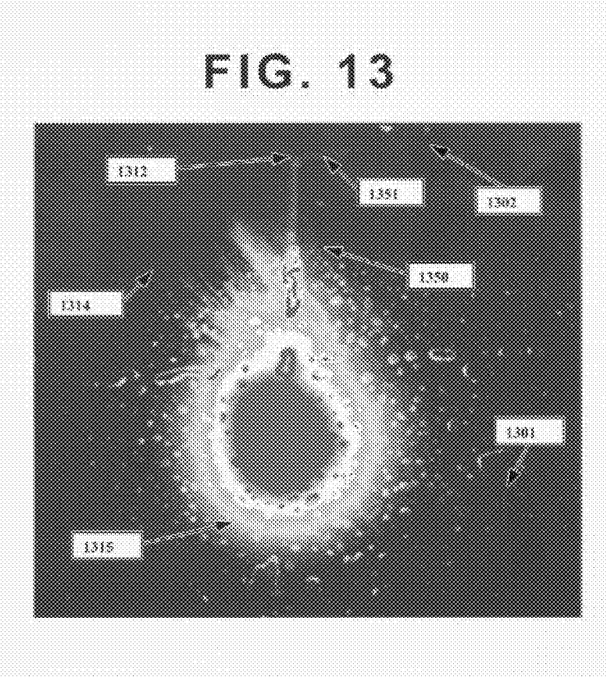
FIG. 13 shows the distribution zone of fluorescent-labeled protein in agarose gel obtained using an 8-port step-catheter and the pulsatile flux pressure regimen of FIG. 6b over 5 days of infusion.

FIG. 13 shows the distribution zone of fluorescent-labeled protein in a section of agarose gel obtained using an 8-port step-catheter and the 25/375/1 pulsatile flux pressure regimen of FIG. 6b over 5 days of infusion. The agarose gel (1301) was sectioned into approximately 2-mm sections to provide a cross-section of the catheter track (1350). The agarose gel (1301) contains a target area (1315) and non-target area (1314) based on the position and placement of the distal end of the catheter, and insertion point (1312) where the catheter was inserted into the surface (1302) of the agarose gel. The image shows the distribution of fluorescent-labeled protein in the target area (1315). The presence of fluorescent-labeled protein along the catheter track (1350) is due to artifact from removal of the catheter. Note that compared with FIG. 4 and also with the target area (1315) there is little or no fluorescent-labeled protein located in the agarose gel surrounding the catheter track (1350) or in non-target area (1314) or in the surrounding agarose gel (1351) near the entry point (1312).

It is an object of the invention to provide a method of delivering a therapeutic fluid to a tissue of a mammal. It is a further object of the invention to provide a method of delivering a therapeutic fluid to a tissue of a mammal whereby the backflow of fluid is prevented and the volume and geometry of the delivery of therapeutic fluid is controlled by applying a regimen of pulsatile delivery matched to a predetermined flux of fluid exiting the catheter. It is a further object of the invention to provide a method of delivering a therapeutic fluid to a tissue of a mammal whereby the backflow of fluid is prevented by calculating the pulsed intervals of fluid flux in the catheter based on the elasticity of the surrounding tissue. It is a further object of the invention to determine the size and number of ports on a delivery catheter to create a predetermined flux and controllable distribution geometry. It is a further object of the invention to provide a method of delivering a therapeutic fluid to a specific tissue of a mammal, wherein said tissue can be brain, liver, kidney, lung, spleen, pancreatic, muscle, or bone tissue.

In one embodiment of the invention, a catheter is inserted into the brain of a mammal, passing through a non-target tissue and into a target tissue. The catheter is operably connected to a drug pump and the drug pump is intermittently operated to generate a pulsatile flux, wherein the drug pump is operated at a constant flow rate for a repetitive periodic cycle of on-off sequences for the duration of required therapy, wherein the pulsatile flux prevents the backflow of therapeutic fluid along the catheter track into the non-target tissue.

In one embodiment of the invention, a catheter is inserted into the brain of a mammal, passing through a non-target tissue and into a target tissue. The catheter is operably connected to a drug pump and the drug pump is intermittently operated to generate a pulsatile flux, wherein the drug pump is operated at a constant flow rate for a repetitive periodic cycle of on-off sequences of 25 seconds on and 375 seconds off for a time period of one hour, after which the drug pump is turned off for a time period of one hour, after which the repetitive periodic cycle of on-off sequences of 25 seconds on and 375 seconds off for a time period of one hour are repeated, after which the drug pump is again turned off for a time period of one hour, and the entire sequence is repeated for the duration of required therapy, wherein the pulsatile flux prevents the backflow of therapeutic fluid along the catheter track into the non-target tissue.

In another embodiment of the invention, a catheter is inserted into the brain of a mammal, passing through a non-target tissue and into a target tissue. The catheter is operably connected to a drug pump and the drug pump is operated to generate a pulsatile flux, wherein the drug pump is operated at variable flow rates ranging between a high and a low flow rate during the operation of the drug pump for a repetitive periodic cycle of higher to lower flow rates for the duration of required therapy, wherein the pulsatile flux created by the variable flow rates prevents the backflow of therapeutic fluid along the catheter track into the non-target tissue.

In another embodiment of the invention, a catheter is inserted into the brain of a mammal, passing through a non-target tissue and into a target tissue. The catheter is operably connected to a drug pump and the drug pump is operated to generate a pulsatile flux, wherein the drug pump is operated at variable flow rates ranging between a high and a low flow rate during the operation of the drug pump for a repetitive periodic cycle of higher to lower flow rates for a time period of one hour, after which the drug pump is turned off for a time period of one hour, after which the repetitive periodic cycle of higher to lower flow rates for a time period of one hour are repeated, after which the drug pump is again turned off for a time period of one hour, and the entire sequence is repeated for the duration of required therapy, wherein the pulsatile flux created by the variable flow rates prevents the backflow of therapeutic fluid along the catheter track into the non-target tissue.

The following examples are included to demonstrate various embodiments of the invention, and are not intended to limit the scope of the invention in any way. It will be appreciated by one skilled in the art that modifications and variations of these specific embodiments to obtain similar results fall within the spirit and scope of the invention.

EXAMPLE 1

Agarose Gel and Fluorescent Labeled Protein Preparation

Agarose gel for all of our studies was made according to the method of Chen, et al. (J Neurosurg 101:314-322, 2004), with the exception that we used PBS (Phosphate Buffered Saline) for the solvent instead of TBE (89 mM Tris; 89 mM boric acid; 2 mM EDTA; and pH 8.4). Thus, one liter of PBS and 6 grams agarose were combined in a one-liter beaker and heated for 5 minutes until the solution became clear. The solution was allowed to cool and then poured into four separate 250-ml beakers and covered with Parafilm until further use.

A stock protein solution of fluorescent-labeled albumin was made using Molecular Probes catalog number A13101 (BSA and Alexa Fluor® 594 conjugate). 5 mg of the fluorescent-labeled albumin was placed into one milliliter of saline solution and stirred to create a 5-mg/ml stock solution, which was kept refrigerated at 2-4° C. until needed. The stock solution was further diluted for use by placing 350-ul of the stock solution into a beaker containing 35-ml of saline solution and stirred to create a 50-ug/ml solution.

EXAMPLE 2

Constant Flow Regimen with Single-Port Step-Catheter

A 250-ml beaker of agarose gel as prepared in example 1 was used for the test media to mimic the distensible tissue. Fluorescent infusate according to example 1 was also used. The distal end of the single-port step-catheter (see FIG. 3) made from GE Ultem 1000F having an outside diameter of 0.800 mm, an inside diameter of 0.630 mm, and a distal portion having an outside diameter of 0.500 mm and an inside diameter of 0.330 mm with a step from 0.630 mm to 0.330 mm, was inserted into a 250-ml beaker of the agarose gel and inserted to a depth of approximately 38 mm from the surface. A plastic holder was fabricated in the shape of a disc having a hole in the center and was placed on the surface of the agarose gel to maintain the position of the catheter. The proximal end of each catheter was connected to a 1.0 ml syringe, which were placed in a programmable syringe pump (Harvard Apparatus model PHD-200). The entire setup including the syringe pump was placed into an oven at 37° C. and allowed to warm to temperature. See FIG. 2.

The syringe pump was turned on and run for 300 minutes at a flow rate of 1 µl per minute, thus the total volume of the fluorescent-labeled protein solution infused was calculated to be 300 µl. After 300 minutes the catheter was removed from the agarose gel and the agarose gel was removed from the beaker. The agarose gel was cut into 2-mm thick sections using a microtome blade, and the distribution of fluorescent-labeled protein was characterized by photographing the gel sections using a LAS-3000 luminescent image analyzer (FujiFilm Life Science). The exposure time was ⅛ second for all images, and the center section image was selected for further examination and analysis.

Now referring to FIG. 4, which shows the distribution zone of fluorescent-labeled protein in a beaker of agarose gel obtained using the single-port step-catheter of FIG. 3 and a constant 1.0 µl/min. flow rate over 300 minutes of infusion. The agarose gel (401) was sectioned into approximately 2-mm sections to provide a cross-section of the catheter track (450). The agarose gel (401) contains a target area (415) and a non-target area (414) based on the position and placement of the distal end of the catheter, and contains an insertion point (412) where the catheter was inserted into the surface (402) of the agarose gel. The image shows the distribution of fluorescent-labeled protein in the target area (415), as well as backflow along the catheter track (450) located in non-target area (414) and into surrounding agarose gel (451) and up to the entry point (412).

EXAMPLE 3

Pulsatile Flux Regimen 25/375/1 Over 24 Hours

The experimental setup was identical to example 2, however different catheters and a different flow regime was used in this example. An 8-port step-catheter (see FIG. 5) was made from GE Ultem 1000F having an outside diameter of 0.800 mm, an inside diameter of 0.630 mm, and a distal portion having an outside diameter of 0.500 mm and an inside diameter of 0.330 mm with 0.25 mm ports, and further having an inside diameter step from 0.630 mm to 0.330 mm. The distal lumen was sealed using Loctite Hysol M-31CL epoxy so that only the ports allowed fluid to exit the catheter. The distal end of the catheter was inserted into a 250-ml beaker of the agarose gel to a depth of approximately 38 mm from the surface. A plastic holder as in example 2 was placed on the surface of the agarose gel to maintain the position of the catheter. The beaker of gel with the catheter was placed into an oven at 37° C. and allowed to warm to temperature, with the proximal end of the catheter connected to a 1.0 ml syringe in a programmable syringe pump, also contained within the oven.

The pulsatile flux dose regimen was selected to have three separate steps. In the first step the syringe pump is on for 25 seconds at a flow rate of 2.7 µl per minute, then for the second step the syringe pump is turned off for 375 seconds (zero flow). Step 3 consists of repeating steps one and two for one hour and then turning off the syringe pump (zero flow) for one entire hour, thus the designation of 25/375/1 to describe the pulsatile flux regimen. This sequence of events is repeated for the 24 hours and is shown in FIG. 6b. The entire setup and experiment was replicated using a 15-port step-catheter (see FIG. 8) instead of the 8-port step-catheter. Thus a 15-port step-catheter (see FIG. 8) was also made from GE Ultem 1000F having an outside diameter of 0.800 mm, an inside diameter of 0.630 mm, and a distal portion having an outside diameter of 0.500 mm and an inside diameter of 0.330 mm with 0.25 mm ports, and further having an inside diameter step from 0.630 mm to 0.330 mm. The distal lumen was sealed using Loctite Hysol M-31CL epoxy so that only the ports allowed fluid to exit the catheter. The distal end of the catheter was also inserted into a 250-ml beaker of agarose gel to a depth of approximately 38 mm from the surface, and a plastic holder as in example 2 was also used to maintain the position of the catheter. The beaker of gel with the catheter was placed into an oven at 37° C. and allowed to warm to temperature, with the proximal end of the catheter connected to a 1.0 ml syringe in a programmable syringe pump, all within the oven.

After 24 hours of running the pulsatile flux regimen the catheters were removed from the agarose gels and the agarose gels were removed from the beakers. The total volume of the fluorescent-labeled protein solution infused was calculated to be 121.5 µl for both experiments. The agarose gels were cut into 2-mm thick sections using a microtome blade and the distribution of fluorescent-labeled protein was characterized by photographing the gel sections using a LAS-3000 luminescent image analyzer (FujiFilm Life Science). The exposure time was ⅛ second for all images, and the center section images were selected for further examination and analysis.

Now referring to FIG. 7, which shows the distribution zone of fluorescent-labeled protein in a section of agarose gel obtained using the 8-port step-catheter and the 25/375/1 pulsatile flux pressure regimen over 24 hours of infusion. The agarose gel (701) contains a target area (715) and a non-target area (714) based on the position and placement of the distal end of the catheter, and contains an insertion point (712) where the catheter was inserted into the surface (702) of the agarose gel. The image shows the distribution of fluorescent-labeled protein in the target area (715). The presence of fluorescent-labeled protein along the catheter track (750) is due to artifact from removal of the catheter. Note that compared with FIG. 4 and also with the target area (715) there is little or no fluorescent-labeled protein located in the agarose gel surrounding the catheter track (750) or in non-target area (714) or in the surrounding agarose gel (751) near the entry point (712). Thus FIG. 7 demonstrates the absence of backflow when using the 25/375/1 pulsatile flux regimen with an 8-port step-catheter over 24 hours.

Now referring to FIG. 9, which shows the distribution zone of fluorescent-labeled protein in a section of agarose gel obtained using the 15-port step-catheter and the 25/375/1 pulsatile flux pressure regimen over 24 hours of infusion. The agarose gel (901) contains a target area (915) and a non-target area (914) based on the position and placement of the distal end of the catheter, and contains an insertion point (912) where the catheter was inserted into the surface (902) of the agarose gel. The image shows the distribution of fluorescent-labeled protein in the target area (915). The presence of fluorescent-labeled protein along the catheter track (950) is due to artifact from removal of the catheter. Note that compared with FIG. 4 and also with the target area (915) there is little or no fluorescent-labeled protein located in the agarose gel surrounding the catheter track (950) or in non-target area (914) or in the surrounding agarose gel (951) near the entry point (912). Thus FIG. 9 demonstrates the absence of backflow when using the 25/375/1 pulsatile flux regimen with a 15-port step-catheter over 24 hours.

EXAMPLE 4

Pulsatile Flux Regimen 40/360/1 Over 24 Hours

In this study we replicated the experimental setup of examples 2 and 3, but instead we used the pulsatile flux pressure regimen shown in FIG. 6d. Thus, instead of using 25 seconds on and 375 seconds off for steps 1 and 2, respectively, we used 40 seconds on and 360 seconds off. Step 3 was maintained at one hour, and the duration of the experiment was also maintained at 24 hours. The same type 8-port and 15-port step-catheters were also used in this experiment. The total volume of infusate was calculated to be 194.4 µl for both catheters in this example.

FIG. 10 shows the distribution zone of fluorescent-labeled protein in a section of agarose gel obtained using an 8-port step-catheter and the 40/360/1 pulsatile flux pressure regimen of FIG. 6d over 24 hours of infusion. The agarose gel (1001) contains a target area (1015) and a non-target area (1014) based on the position and placement of the distal end of the catheter, and contains an insertion point (1012) where the catheter was inserted into the surface (1002) of the agarose gel. The image shows the distribution of fluorescent-labeled protein in the target area (1015). The presence of fluorescent-labeled protein along the catheter track (1050) is due to artifact from removal of the catheter. Note that compared with FIG. 4 and also with the target area (1015) there is little or no fluorescent-labeled protein located in the agarose gel surrounding the catheter track (1050) or in non-target area (1014) or in the surrounding agarose gel (1051) near the entry point (1012). Thus FIG. 10 demonstrates the absence of backflow when using the 40/360/1 pulsatile flux regimen and an 8-port step-catheter over 24 hours.

FIG. 11 shows the distribution zone of fluorescent-labeled protein in a section of agarose gel obtained using a 15-port step-catheter and the 40/360/1 pulsatile flux pressure regimen over 24 hours of infusion. Although the agarose gel (1101) was similarly sectioned into approximately 2-mm sections to provide a cross-section of the catheter track (1150), the location of the sectioning in this example did not provide a clear indication of the void space of the catheter track. The agarose gel (1101) contains a target area (1115) and a non-target area (1114) based on the position and placement of the distal end of the catheter, and an insertion point (1112) where the catheter was inserted into the surface (1102) of the agarose gel. The image shows the distribution of fluorescent-labeled protein in the target area (1115). Note that compared with FIG. 4 and also with the target area (1115) there is little or no fluorescent-labeled protein located in the agarose gel surrounding the catheter track (1150) or in non-target area (1114) or in the surrounding agarose gel (1151) near the entry point (1112). Thus FIG. 11 also demonstrates the absence of backflow when using the 40/360/1 pulsatile flux regimen and a 15-port step-catheter over 24 hours.

EXAMPLE 5

Pulsatile Flux Regimen 25/375/1 for 76 Hours

In this study we replicated the setup of example 3 using the 25/375/1 regimen, but instead we increased the duration of the experiment to 76 hours using a pair of 15-port step-catheters (no 8-port catheter was employed in this experiment). The total volume of infusate was calculated to be 384 µl for both catheters in this example.

FIGS. 12a and 12b show the distribution zones of fluorescent-labeled protein in sections of agarose gel obtained using two different 15-port step-catheters and the 25/375/1 pulsatile flux pressure regimen of FIG. 6b over 76 hours of infusion. The agarose gels (1201a,b) were sectioned into approximately 2-mm sections to provide cross-sections of the catheter tracks (1250a,b). The agarose gels (1201a,b) contain target areas (1215a,b) and non-target areas (1214a,b) based on the position and placement of the distal ends of the catheters, and contain insertion points (1212a,b) where the catheters were inserted into the surface (1202a,b) of the agarose gels. The images show the distributions of fluorescent-labeled protein in the target areas (1215a,b). The presence of fluorescent-labeled protein along the catheter tracks (1250a, b) is due to artifact from removal of the catheters. Note that compared with FIG. 4 and also with the target areas (1215a,b) there is little or no fluorescent-labeled protein located in the agarose gel surrounding the catheter tracks (1250a,b) or in non-target areas (1214a,b) or in the surrounding agarose gel (1251a,b) near the entry points (1212a,b). Thus FIGS. 12a and 12b demonstrate the absence of backflow when using the 25/375/1 pulsatile flux regimen and 15-port step-catheters over 76 hours.

EXAMPLE 6

Pulsatile Flux Regimen 25/375/1 for 5 Days

In this study we replicated the experimental setup of example 3 using an 8-port step-catheter and increased the duration to 5 days. The total volume of infusate was calculated to be 607 µl in this example.

FIG. 13 shows the distribution zone of fluorescent-labeled protein in a section of agarose gel obtained using an 8-port step-catheter and the 25/375/1 pulsatile flux pressure regimen over 5 days of infusion. The agarose gel (1301) was sectioned into approximately 2-mm sections to provide a cross-section of the catheter track (1350). The agarose gel (1301) contains a target area (1315) and non-target area (1314) based on the position and placement of the distal end of the catheter, and insertion point (1312) where the catheter was inserted into the surface (1302) of the agarose gel. The image shows the distribution of fluorescent-labeled protein in the target area (1315). The presence of fluorescent-labeled protein along the catheter track (1350) is due to artifact from removal of the catheter. Note that compared with FIG. 4 and also with the target area (1315) there is little or no fluorescent-labeled protein located in the agarose gel surrounding the catheter track (1350) or in non-target area (1314) or in the surrounding agarose gel (1351) near the entry point (1312). Thus FIG. 13 demonstrates the absence of backflow when using the 25/375/1 pulsatile flux regimen and an 8-port step-catheter over the course of 5 days.

These examples are included to demonstrate various embodiments of the invention, and are not intended to limit the scope of the invention in any way. It will be appreciated by one skilled in the art that modifications and variations of these specific embodiments to obtain similar results fall within the spirit and scope of the invention.

We claim:

1. A method of treating a mammal comprising the steps of:
   a. introducing a catheter into a distensible tissue of a mammal, said catheter being operably connected to a drug delivery pump, and
   b. intermittently operating said drug delivery pump for one or more predetermined intervals of time to generate a pulsatile flux of drug through said catheter into said tissue, wherein said time intervals of intermittent pump operation allow sufficient time for said distensible tissue to recoil around said catheter, thereby preventing backflow of said drug along an outer wall of said catheter.

2. The method of claim 1, wherein said one or more predetermined time intervals of pump operation are comprised of equal intervals of operational and non-operational time intervals.

3. The method of claim 1, wherein said one or more predetermined time intervals of pump operation are comprised of non-equal time intervals of operational and non-operational time intervals.

4. The method of claim 3 wherein the non-operational time intervals are greater than the operational time intervals.

5. The method of claim 1, wherein said one or more predetermined time intervals of pump operation are comprised of two or more different intervals of non-operational time intervals.

6. The method of claim 1, wherein said one or more predetermined time intervals of pump operation are comprised of two or more different time intervals of pump operation.

7. The method of claim 1, wherein said one or more predetermined time intervals of pump operation are comprised of two or more different intervals of operational time intervals and two or more non-operational time intervals.

8. The method of claim 1, wherein said one or more predetermined time intervals of pump operation are repetitively performed to generate a pulsatile flux of drug exiting the catheter into said tissue.

9. The method of claim 1 further comprised of the step of controlling the flux exiting the catheter by altering a number and size of ports on said catheter.

10. The method of claim 1 wherein said distensible tissue is selected from the group consisting of brain, liver, kidney, lung, spleen, and pancreatic tissue.

11. The method of claim 10 wherein said distensible tissue is brain tissue.

12. A method of treating a mammal comprising the steps of:
    a. introducing a catheter into a distensible tissue of a mammal, said catheter being operably connected to a drug delivery pump, and
    b. operating said drug delivery pump at two or more predetermined rates of flow over two or more predetermined time intervals to generate a pulsatile flux of drug through said catheter into said tissue, wherein the combination of said two or more predetermined rates of flow over two or more predetermined time intervals allow sufficient time for said distensible tissue to recoil around said catheter, thereby preventing backflow of said drug along an outer wall of said catheter.

13. The method of claim 12 wherein said distensible tissue is selected from the group consisting of brain, liver, kidney, lung, spleen, and pancreatic tissue.

14. The method of claim 13 wherein said distensible tissue is brain tissue.

* * * * *